US00PP32454P2

(12) United States Plant Patent
Holtmaat

(10) Patent No.: US PP32,454 P2
(45) Date of Patent: Nov. 10, 2020

(54) ***RUDBECKIA* PLANT NAMED 'RUBSOL'**

(50) Latin Name: *Rudbeckia hirta*
Varietal Denomination: Rubsol

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/602,275

(22) Filed: Sep. 5, 2019

(30) Foreign Application Priority Data

Aug. 5, 2019 (QZ) ..... PBR 20191915

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 6/14
See application file for complete search history.

*Primary Examiner* — Anne Marie Grunberg
(74) *Attorney, Agent, or Firm* — Penny J. Aguirre

(57) ABSTRACT

A new cultivar of hybrid *Rudbeckia* plant, 'Rubsol', characterized by its short plant habit in the first 3 months and becoming broader and taller which is desirable to hold the abundance of blooms, its narrow leaves, its very floriferous blooming habit, its small flowers, and its inflorescences with ray floret that are orange-yellow in color with a purplish brown base.

2 Drawing Sheets

Botanical classification: *Rudbeckia hirta.*
Variety denomination: 'Rubsol'.

CROSS REFERENCE TO A RELATED APPLICATION

This application claims priority to European Community Plant Variety Office (CPVO) Plant Breeder's Rights Application No. 2019/1915 filed on Aug. 5, 2019, the entire contents of which is incorporated by reference herein.

BACKGROUND OF THE INVENTION

The present invention relates to a new and distinct cultivar of *Rudbeckia* of hybrid origin. The new *Rudbeckia* will hereafter by its cultivar name, 'Rubsol'. The new cultivar is grown for use as a landscape plant.

'Rubsol' was derived from a breeding program conducted by the Inventor at a nursery in Zuidwolde, The Netherlands. The object of the breeding program was to select a new cultivar of *Rudbeckia* with a floriferous blooming habit and a compact plant habit.

'Rubsol' was selected in July of 2017 by the Inventor from amongst seedlings in a trial field that had been planted with seed numerous plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in January 2018. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosure include but may not be limited to website listings related to entrance in the new plant competition at Plantarium.

SUMMARY OF THE INVENTION

The following traits have been repeatedly observed and represent the characteristics of the new cultivar. These attributes in combination distinguish 'Rubsol' as a unique cultivar of *Rudbeckia.*

1. 'Rubsol' exhibits a short plant habit in the first 3 months and becoming broader and taller which is desirable to hold the abundance of blooms.
2. 'Rubsol' exhibits narrow leaves.
3. 'Rubsol' exhibits a very floriferous blooming habit.
4. 'Rubsol' exhibits small flowers.
5. 'Rubsol' exhibits inflorescences with ray floret that are orange-yellow in color with a purplish brown base.

'Rubsol' can be compared to the *Rudbeckia* cultivars 'RUDHT19' (not patented), and 'RUDHT55' (U.S. Plant Pat. No. 30,726). 'RUDHT19' is similar to 'Rubsol' in plant height. 'RUDHT19' differs from 'Rubsol' in having ray floret colors that are dark purplish brown with yellow tips and in having a less floriferous blooming habit. 'RUDHT55' is similar to 'Rubsol' in having leaves that are similar in shape. 'RUDHT55' differs from 'Rubsol' in having a taller plant height, ray floret colors that are dark purplish brown with orange tips and in having a much less floriferous blooming habit.

BRIEF DESCRIPTION OF THE DRAWINGS

The accompanying colored photographs illustrate the overall appearance and distinct characteristics of the new *Rudbeckia*. The photographs were taken of a one-year-old plant of 'Rubsol' as grown outdoors in a 21-cm containers in Zuidwolde, The Netherlands.

The photograph in FIG. 1 is a side view of 'Rubsol' in bloom.

Figure 1:
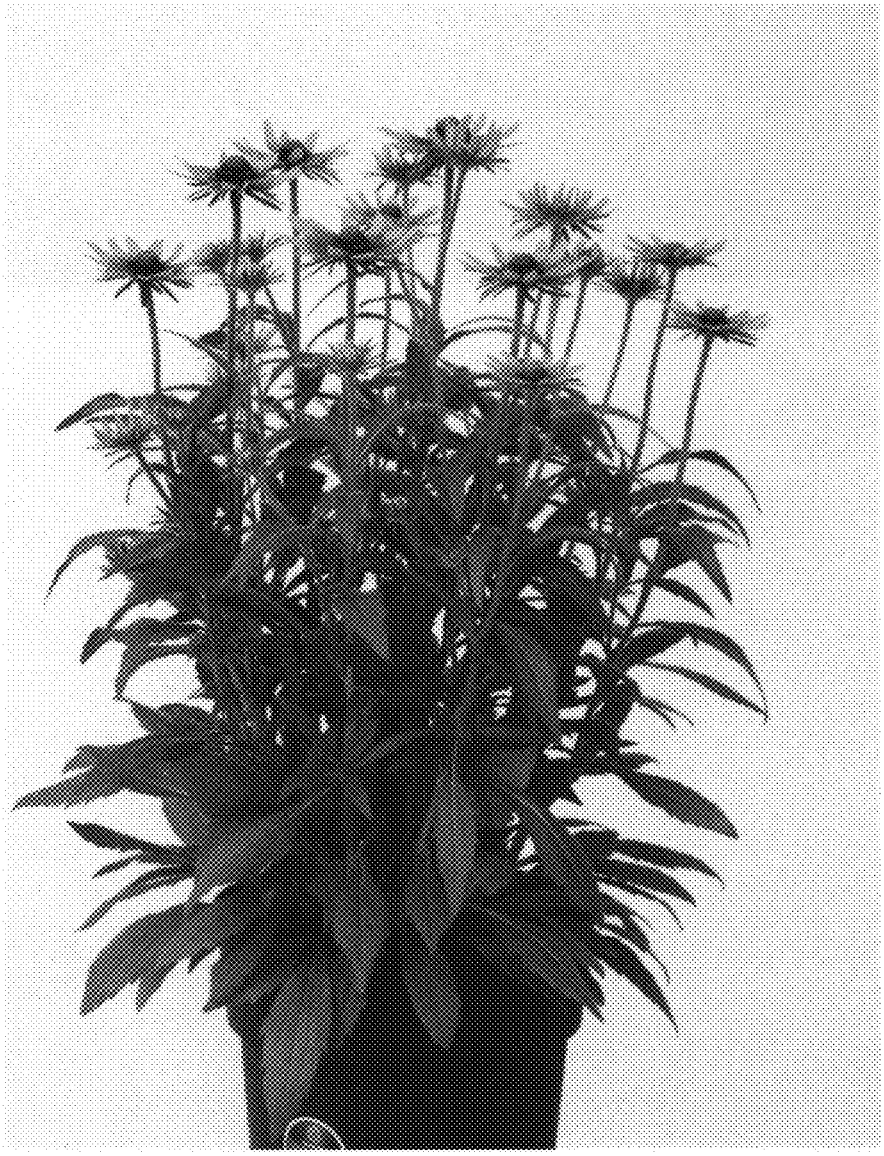
Figure 2:
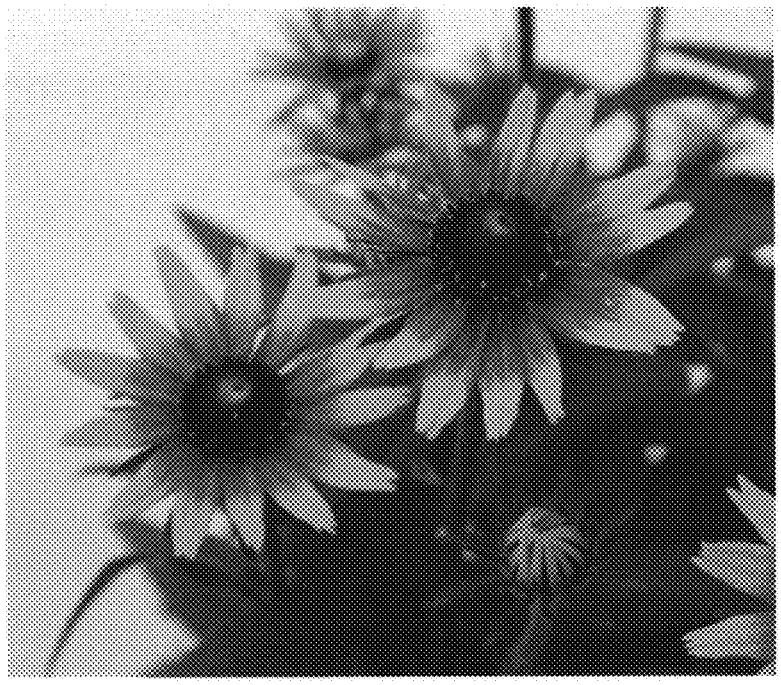

The photograph in FIG. 2 provides a close-up view of the inflorescences of 'Rubsol'.

Figure 3:
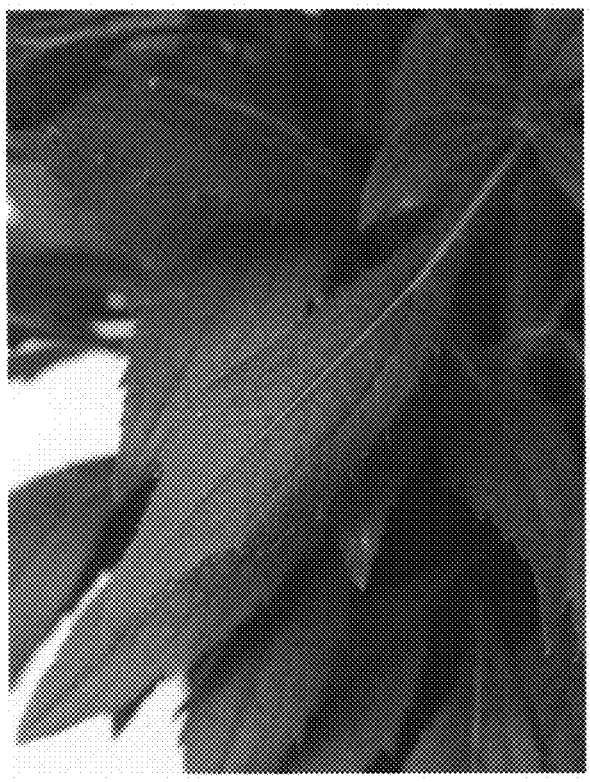

The photograph in FIG. 3 provides a close-up view of the foliage of 'Rubsol'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of one-year-old plants of 'Rubsol' as grown outdoors in 21-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 10 weeks from June until mid-September in the Netherlands.

*Plant type*.—Perennial.

*Plant habit*.—Upright, compact.

*Plant shape*.—Narrow obovate.

*Height and spread*.—Average of 42.2 cm in height from soil level to top of foliar plane and 53.1 cm in height from soil level to top of floral plane, 42.5 cm in diameter.

*Hardiness*.—At least in U.S.D.A. Zones 4 to 10.

*Diseases and pests*.—No susceptibility and resistance to diseases or pests has been observed.

*Root description*.—Fine and fibrous.

*Propagation*.—Tissue culture.

*Root development*.—An average of 10 weeks for root initiation with a young rooted plant produced in an average of 3 months.

*Growth rate and vigor*.—Moderate.

Stem description:

*Shape*.—Slightly angled.

*Stem color*.—Young stems; 144B, mature stems; 144A to 144B, 143B to 143C at the angles, 144A to 144B at the internodes.

*Stem size*.—An average of 4 mm in diameter and an average of 33.3 cm in height.

*Stem surface*.—Moderately glossy and densely covered with strigose hairs an average of 2 mm in length and close to N155A in color.

*Stem number*.—Average of 15 main stems, 2 lateral branches per main stem.

*Internode length*.—An average of 3.5 cm in length.

*Stem aspect*.—Main stems; average of 22.5° to vertical, lateral branches; average of 25° to main stems.

*Branching*.—Freely branching from base with lateral stems.

Foliage description:

*Leaf shape*.—Narrowly elliptic.

*Leaf division*.—Simple.

*Leaf base*.—Cuneate.

*Leaf apex*.—Acute.

*Leaf venation*.—Pinnate, color on upper and lower surface 145B.

*Leaf margins*.—Coarsely serrate, non-undulate.

*Leaf attachment*.—Petiolate.

*Leaf arrangement*.—Alternate.

*Leaf size*.—Average of 12 cm in length and 3.3 cm in width.

*Leaf color*.—Young upper surface; 137B, young lower surface; 138B, mature upper surface; 137A, mature lower surface; a color between 137D to 138A.

*Leaf surface*.—Upper surface matte, and non-rugose, rough to touch, lower surface is matte, slightly rugose, rough to touch, both surfaces densely pubescent with short strigose hairs; an average of 1.75 mm in length and N155A in color.

*Petioles*.—Average of 3.6 cm in length, flattened, average diameter at widest point 4.5 and at narrowest point 2.5 mm, upper surface color; 147D with margins 137A, lower surface color; 145A to 145B with margins 137B, both surfaces slightly glossy and densely covered with strigose hairs; am average of 1.75 in length and N155A in color.

Flower description:

*Type*.—Terminal capitulum, consisting of ray florets and disc florets.

*Capitulum number*.—3 per stem, up to 48 per plant.

*Lastingness of inflorescence*.—Average of 2 weeks, persistent.

*Capitulum size*.—Matures to about 3.6 cm in height and 8.3 cm in diameter, disk size is an average of 2.5 cm in diameter.

*Fragrance*.—None.

*Involucral bracts* (*phyllaries*).—Broadly cuneate base, acute apex, narrow oblong to oblanceolate in shape, entire margins, average of 24 arranged in two rows, 2.6 cm in length and 3 mm in width, color; upper surface when fully open 137A, lower surface when fully open 137D, both surfaces matt and densely covered with strigose hairs; an average of 1.5 mm in length and N155A in color.

*Receptacle*.—Broadly ovate in shape, an average of 1.3 cm in height and 1 cm in diameter, 157C to 157D in color.

*Bracts*.—1 at each disc floret, spirally placed on disc, soft, flattened, an average of 6 mm in length and 1 mm in diameter, oblanceolate in shape, acute apex, narrowly cuneate in shape, color; apex 176A, mid-section 145D to 157A, base 157B, matte surface and moderately pubescent with hairs; an average of 0.4 mm in length and 182D in color.

*Buds*.—Globular in shape, immature ray florets pointed upward and curling inward, up to 2.3 cm in length and 4.1 cm in diameter, immature ray florets are 150B in color, immature involucral bracts upper surface 137B, lower surface 138A, surface on involucral bracts is densely covered with strigose hairs; an average of 2 mm in length and N155A, surface on immature ray florets; adpressed hairs an average of 0.75 mm in length and 155A in color.

*Peduncle*.—Strong, straight on top of main flowering stem, average of 13.2 cm in length and 4.5 mm in diameter, color; 144A and axially striped 143A, surface slightly glossy sand densely covered with short strigose hairs; an average of 2 mm in length and N155A in color.

*Ray florets*.—Average of 15 (varying between 13 and 17), rotate around the disc, lanceolate in shape, average of 3.8 cm in length and 1 cm in width, praemorse apex, cuneate base, entire margin, both surfaces are velvety, matte and glabrous, held near horizontal, color; when opening upper surface 14B, lower half 17B, when opening lower surface 153D, when fully open upper surface 17B, changing to 185A at the base, when fully open lower surface 14B, changing to 20A at the base with veins 145A.

*Disk flowers*.—Average about 1,000, slightly curved and tubular in shape, arranged spirally on a conical receptacle, lower 90% fused into tube, upper 10% free, about 8 mm in length and 4 mm in width, free lobes have entire margins, both surfaces glabrous and moderately glossy, color; when opening upper and lower surface 203A, mid-section 200A, base 157D, when fully open upper and lower surface 203A, changing to 200A and 203A, mid-section 200A, changing to 182D towards the base, 157D at the base.

Reproductive organs:

*Gynoecium*.—Pistil; 1, 7 mm in length, style; 5 mm in length, 200A in color, mid-section 155C and tinged 187C with base 155C, stigma; cleft, decurrent, 4 mm in diameter, 200A in color, ovary; NN155C in color.

*Androcoecium*.—Stamens; 5, filaments; 2 mm in length, 160D in color, anther; narrow oblong in shape, 3 mm in length, 0.5 mm in width, 200A in color, pollen; abundant to moderate in quantity and 21A in color.

*Fruit/seed*.—None observed.

It is claimed:

1. A new and distinct cultivar of *Rudbeckia* plant named 'Rubsol' substantially as herein illustrated and described.

* * * * *